(12) United States Patent
Lee

(10) Patent No.: US 8,021,328 B2
(45) Date of Patent: Sep. 20, 2011

(54) RAPID EXCHANGE INFUSION CATHETER

(75) Inventor: Jeong S. Lee, Diamond Bar, CA (US)

(73) Assignee: Abbott Cardiocascular Systems Inc., Santa Clara, CA (US)

( * ) Notice: Subject to any disclaimer, the term of this patent is extended or adjusted under 35 U.S.C. 154(b) by 148 days.

(21) Appl. No.: 11/682,104

(22) Filed: Mar. 5, 2007

(65) Prior Publication Data

US 2008/0221550 A1 Sep. 11, 2008

(51) Int. Cl.
*A61M 29/00* (2006.01)

(52) U.S. Cl. .............. 604/96.01; 604/509; 604/103.04

(58) Field of Classification Search ............ 604/97.01, 604/96.01, 103.04, 508–510
See application file for complete search history.

(56) References Cited

U.S. PATENT DOCUMENTS

| | | | |
|---|---|---|---|
| 5,201,315 A | 4/1993 | Griffith | |
| 5,203,338 A | 4/1993 | Jang | |
| 5,219,335 A | 6/1993 | Willard | |
| 5,249,580 A | 10/1993 | Griffith | |
| 5,320,604 A | 6/1994 | Walker | |
| 5,327,885 A | 7/1994 | Griffith | |
| 5,458,099 A | 10/1995 | Koller | |
| 5,458,613 A | 10/1995 | Gharibadeh | |
| 5,514,092 A | 5/1996 | Forman | |
| 5,545,138 A | 8/1996 | Fugoso | |
| 5,755,685 A | 5/1998 | Andersen | |
| 6,027,474 A * | 2/2000 | Douk et al. | 604/95.01 |
| 6,027,487 A | 2/2000 | Crocker | |
| 6,264,632 B1 * | 7/2001 | Jang | 604/97.01 |
| 6,458,099 B2 | 10/2002 | Dutta | |
| 6,827,710 B1 * | 12/2004 | Mooney et al. | 604/500 |
| 6,966,890 B2 | 11/2005 | Coyle | |
| 6,997,899 B2 * | 2/2006 | Scopton | 604/103.04 |
| 2003/0014008 A1 * | 1/2003 | Jacques | 604/96.01 |
| 2003/0120208 A1 | 6/2003 | Houser | |
| 2005/0027249 A1 * | 2/2005 | Reifart et al. | 604/103.04 |
| 2005/0267442 A1 * | 12/2005 | Von Oepen | 604/509 |

* cited by examiner

*Primary Examiner* — Theodore Stigell
*Assistant Examiner* — Brandy C Scott
(74) *Attorney, Agent, or Firm* — Fulwider Patton LLP; Thomas H. Majcher, Esq.

(57) ABSTRACT

An infusion catheter and method, with an elongated shaft having a guidewire lumen which has a proximal section and a common distal section extending to a distal port at a distal end of the shaft, and an infusion lumen which is in fluid communication with the distal port of the guidewire lumen and which joins the common distal section of the guidewire lumen at a location distal to the guidewire proximal port. A restricted passage from the infusion lumen to the common distal section of the guidewire lumen has a smaller transverse dimension than the guidewire lumen and a guidewire slidably disposed in the guidewire lumen.

13 Claims, 3 Drawing Sheets

RAPID EXCHANGE INFUSION CATHETER

CROSS-REFERENCES TO RELATED APPLICATIONS

None

BACKGROUND OF THE INVENTION

The present invention relates generally to medical devices, and more particularly to a catheter for delivery of an agent to the coronary or peripheral vasculature.

In the treatment of diseased vasculature, therapeutic agents have commonly been administered, typically as part of other interventional therapies such as angioplasty or stent delivery. Local, as opposed to systemic delivery is a preferred method of treatment in that smaller total levels of medication are administered in comparison to systemic dosages, yet are concentrated at a specific site. As a result, local delivery produces fewer side effects and achieves more effective results.

A variety of methods and devices have been proposed for percutaneous drug delivery to a diseased region of the vasculature. For example, the catheter shaft can have a drug delivery lumen which extends to a port in the distal end of the catheter, and which is connected at the proximal end to a fluid source containing the drug. In catheters having porous balloons, the drug can be infused either through the inflation lumen or a separate, dedicated drug delivery lumen in the catheter shaft, into the inflatable interior of the porous balloon and through the porous wall of the balloon.

In order to properly position the distal end of a drug delivery catheter in a patient's tortuous distal vasculature, the catheter should preferably have good force transmission, and a low-profile, flexible distal section, to advance within the patient's body lumen. The catheter is typically advanced into position by pushing the proximal end of the catheter and tracking the catheter over a guidewire. However, one difficulty has been providing a drug delivery catheter with a relatively large drug delivery lumen for infusion of the drug, which is nonetheless highly maneuverable (e.g., pushability and trackability) to facilitate positioning the catheter at the desired treatment location in the patient's vasculature.

SUMMARY OF THE INVENTION

The invention is directed to an infusion catheter with an elongated shaft having a guidewire lumen which has a proximal section and a common distal section extending to a distal port at a distal end of the shaft, and an infusion lumen which is in fluid communication with the distal port of the guidewire lumen and which joins the common distal section of the guidewire lumen at a location distal to the guidewire proximal port. The catheter is configured to prevent or inhibit a guidewire from slidably extending between the infusion and guidewire lumens. The configuration provides a highly maneuverable shaft with an improved combination of low-profile, flexibility, and a relatively large lumen size for rapid infusion.

In a presently preferred embodiment, the infusion catheter is a balloon catheter having an inflatable balloon on a distal section of the shaft. The infusion balloon catheter generally comprises an elongated shaft having a proximal end, a distal end, an inflation lumen in fluid communication with an interior of the inflatable balloon, a guidewire lumen, and an infusion lumen. The guidewire lumen has a proximal section and a common distal section, and extends from a guidewire distal port at the shaft distal end to a guidewire proximal port spaced distally from the proximal end of the shaft. The infusion lumen is in fluid communication with the guidewire distal port, and extends alongside the proximal section of the guidewire lumen and proximally of the guidewire proximal port to the proximal end of the shaft. The infusion lumen joins the common distal section of the guidewire lumen at a location distal to the guidewire proximal port and proximal to a distal end of the inflation lumen.

Preferably, the passage from the infusion lumen to the common distal section of the guidewire lumen has a shape which provides a relatively large volume for infusion of the agent while at the same time restricting (e.g., preventing) passage of a guidewire therethrough. In a presently preferred embodiment, the restricted passage has a crescent-shape. The catheter is slidably disposed on a guidewire, typically by being back-loaded over the guidewire either before or after the guidewire is positioned in the patient's body lumen. Thus, the guidewire proximal end is threaded into the guidewire distal port, through the guidewire lumen, and out guidewire proximal port, and the catheter shaft design facilitates the ability to back-load the catheter onto the guidewire with the guidewire proximal end prevented or inhibited from entering the infusion lumen by the restricted, e.g., crescent-shaped, passage. The restricted passage can have a variety of suitable shapes, but by having a transverse dimension in at least one direction that is smaller than the guidewire (and thus smaller than the guidewire lumen as well), the restricted passage will prevent the guidewire from sliding into the infusion lumen.

The distal section of the guidewire lumen is commonly shared, in that it is used to accommodate a guidewire and to infuse an agent. As a result the catheter shaft maintains a flexible, low profile with a round tip configuration, unlike infusion catheters having two separate lumens extending side-by-side to the distal tip of the catheter for the guidewire and for infusion. Moreover, a catheter shaft of the invention is configured to provide relatively large sized lumens, including the infusion lumen to facilitate a fast rate of infusion. In contrast, attempts to minimize the profile increase caused by the addition of a separate infusion lumen by minimizing the size of the infusion lumen along the distal end of the catheter can disadvantageously increase the time required to perform the medical procedure.

In a method of performing a medical procedure in a patient's body lumen, an infusion balloon catheter of the invention is advanced within the patient's body lumen, and a fluid delivered to the body lumen from the catheter infusion lumen. The method generally comprises advancing within the patient's body lumen an infusion balloon catheter comprising an elongated shaft having a proximal end, a distal end, an inflation lumen, a guidewire lumen which has a proximal section and a common distal section and which extends from a guidewire distal port at the shaft distal end to a guidewire proximal port spaced distally from the proximal end of the shaft, and an infusion lumen which is in fluid communication with the guidewire distal port and which extends alongside the proximal section of the guidewire lumen and proximally of the guidewire proximal port to the proximal end of the shaft, and which joins the common distal section of the guidewire lumen at a location distal to the guidewire proximal port and proximal to a distal end of the inflation lumen, and a balloon on a distal section of the elongated shaft having an interior in fluid communication with the inflation lumen. The distal end of the shaft is positioned at a desired location in the body lumen, with a guidewire slidably disposed in the guidewire lumen, the guidewire having a proximal end and a distal end and extending from the guidewire proximal port to the guidewire distal port. In a presently preferred embodiment, when ready to infuse the agent, the guidewire is proximally retracted relative to the shaft, to position the distal end of the guidewire at the proximal section of the guidewire lumen. As a result, the guidewire will not obstruct the flow of the agent through the common distal section of the guidewire lumen. Moreover, the guidewire preferably prevents or inhibits the back-flow of the agent proximally out the guidewire proximal port through the proximal section of the guidewire lumen. The method thus preferably includes delivering a fluid to the patient's body lumen with the guidewire in the proximally retracted position, by infusing the fluid through the infusion lumen, to the common distal section of the guidewire lumen, and then out the guidewire distal port. After the infusion, the catheter can be withdrawn proximally from the body lumen with the guidewire or alternatively leaving the guidewire in place in the body lumen, or the guidewire can be advanced distally through the common distal section of the guidewire lumen if desired before the catheter is repositioned or removed from the body lumen.

A catheter of the invention balances the often competing considerations of low profile, maneuverability, and large lumen size, to provide an infusion catheter with improved performance. These and other advantages of the invention will become more apparent from the following detailed description of the invention and accompanying exemplary drawings.

DETAILED DESCRIPTION OF THE PREFERRED EMBODIMENTS

Figure 1:
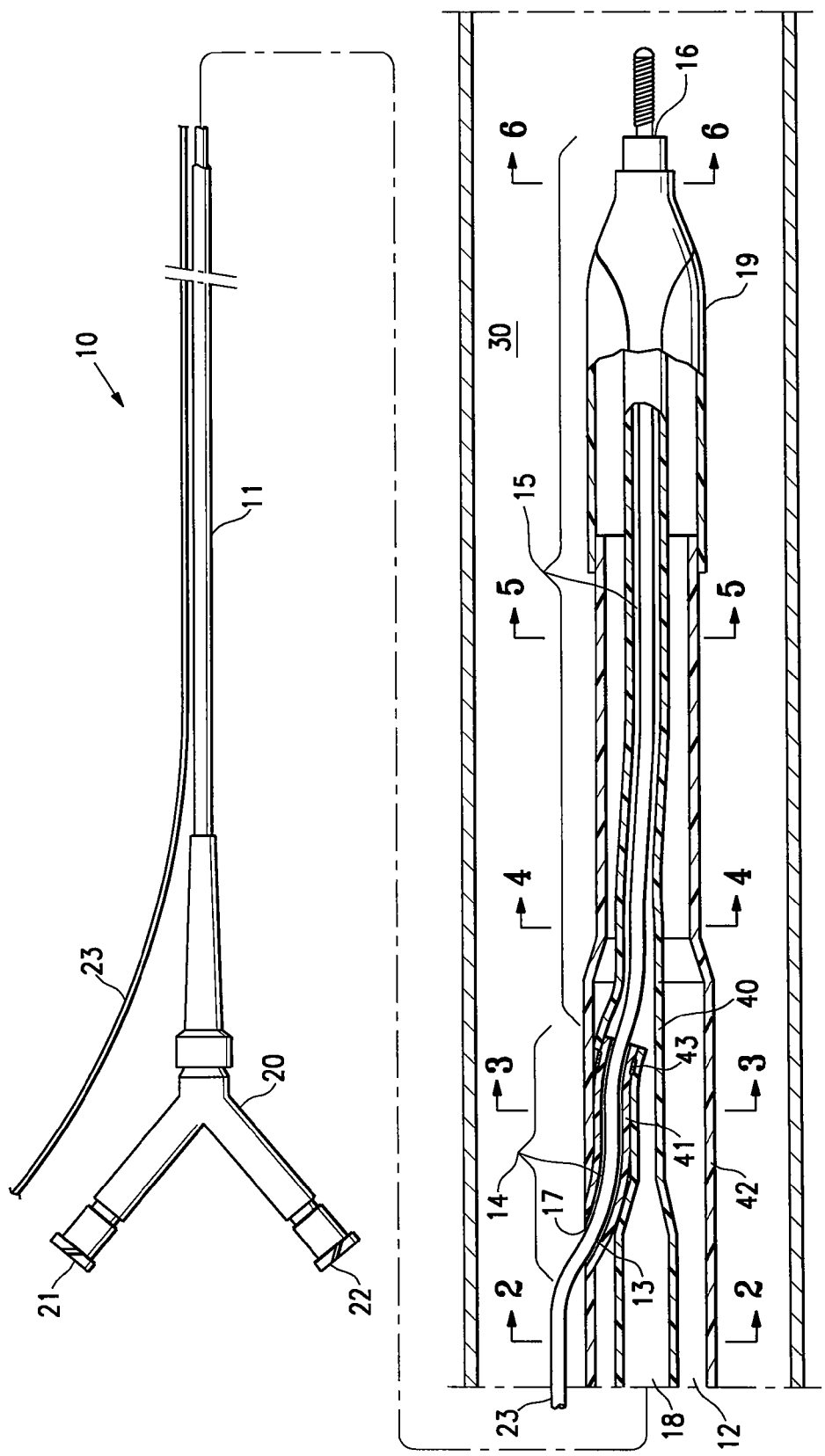
FIG. 1 is an elevational, partially in section, view of an infusion balloon catheter embodying features of the invention, on a guidewire within a patient's body lumen.
Figure 2:
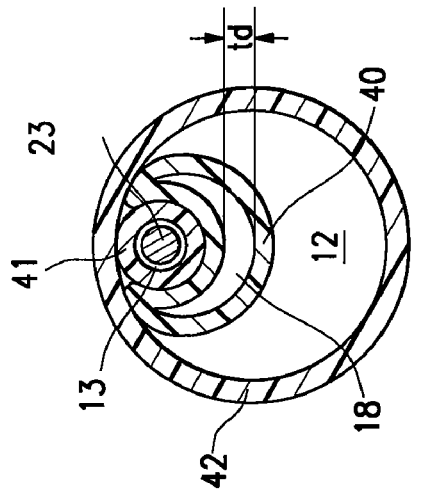
FIGS. 2-6 are transverse cross sections of the catheter of FIG. 1, taken along lines 2-2, 3-3, 4-4, 5-5, and 6-6, respectively.

FIG. 1 illustrates an elevational, partially in section, view of an infusion balloon catheter 10 embodying features of the invention, generally comprising an elongated shaft 11 having a proximal end, a distal end, an inflation lumen 12, a guidewire lumen 13 which has a proximal section 14, a common distal section 15, and a distal port 16, and an infusion lumen 18 which is in fluid communication with the guidewire lumen distal port 16. An inflatable balloon 19 is on a distal section of the shaft, and has an interior in fluid communication with the inflation lumen 12. The catheter is a rapid exchange type catheter in that the guidewire lumen 13 extends from the distal port 16 at the shaft distal end to a guidewire proximal port 17 spaced distally from the proximal end of the shaft. A proximal adapter 20 on the proximal end of the catheter shaft 11 has a first arm with a port 21 which is in fluid communication with the inflation lumen 12 and which is configured to connect to an inflation fluid source (not shown), and a second arm with a port 22 which is in fluid communication with the infusion lumen 18 and which is configured to connect to a fluid agent source (not shown). The infusion balloon catheter 10 can be advanced to a desired treatment location within a patient's body lumen 30, and the balloon inflated and an agent infused into the body lumen 30 to perform a medical procedure, and then the balloon deflated to allow for repositioning or removal of the catheter 10 from the body lumen 30. The balloon 19 is typically configured to anchor the catheter 10 in the body lumen 30 by inflating the balloon 19 before or during infusion of the agent. However, the balloon 19 can be configured for a variety of suitable additional or alternative uses including dilation, or stent delivery with a stent (not shown) releasably mounted thereon. FIG. 1 illustrates the catheter 10 with the balloon 19 in a low profile noninflated configuration for advancement within the body lumen 30, and with a guidewire 23 slidably disposed in the guidewire lumen 13. FIGS. 2-6 illustrate transverse cross sections of the catheter 10 of FIG. 1, taken along lines 2-2, 3-3, 4-4, 5-5, and 6-6, respectively.

The infusion lumen 18 extends alongside (i.e., side-by-side with) the proximal section 14 of the guidewire lumen 13 and proximally of the guidewire proximal port 17 to the proximal end of the shaft. The infusion lumen 18 feeds into and thereby joins the common distal section 15 of the guidewire lumen 13 at a location distal to the guidewire proximal port 17 and proximal to a distal end of the inflation lumen 12, with a restricted passage from the infusion lumen 18 to the common distal section 15 of the guidewire lumen 13 having a smaller inner transverse dimension than the guidewire lumen 13. Thus, the common distal section 15 of the guidewire lumen 13 acts as the single lumen conduit which connects the distal port 16 with both the infusion lumen 18 and the proximal section 14 of the guidewire lumen 13, and the restricted passage is configured to prevent or inhibit the guidewire 23 from slidably extending therethrough between the infusion lumen 18 and the guidewire lumen 13. Typically, the entire length of the guidewire lumen 13 has a larger diameter/transverse dimension than the restricted passage to the infusion lumen 18.

Figure 3:
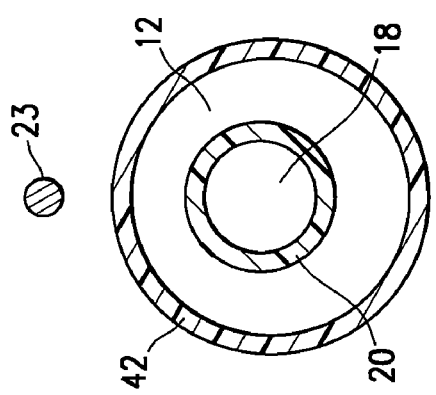
Figure 6:
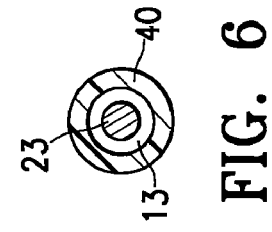
Figure 5:
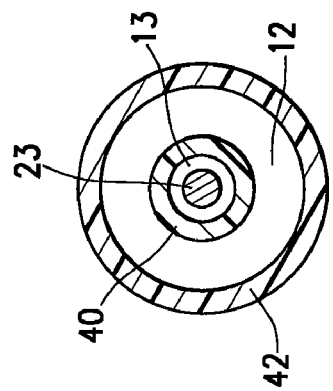
Figure 4:
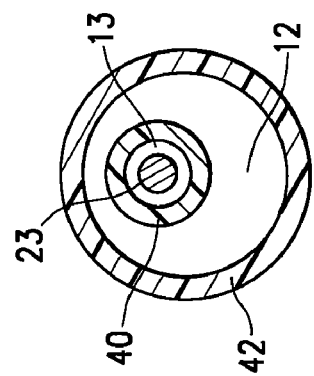

In a presently preferred embodiment, the restricted passage from the infusion lumen 18 to the guidewire lumen 13 is formed by a distal end section of the infusion lumen 18, alongside the guidewire lumen proximal section 14, which has a transverse cross sectional shape which is noncircular. The noncircular shape of the distal end section of the infusion lumen preferably maximizes the lumen volume available for infusion of a fluid, but in a way which does not accommodate or correspond to the round shape of the outer surface of the guidewire 20. In the illustrated embodiment, the noncircular restricted passage of the infusion lumen 18 has a crescent shape, as best shown in FIG. 3 illustrating a transverse cross section of the catheter of FIG. 1, through the distal end section of the infusion lumen 18 along line 3-3. The crescent-shaped section of the infusion lumen 18 has an inner transverse dimension (td) (see FIG. 3) in a first direction which preferably is too small to allow entry of the guidewire 23. For example, as the guidewire 23 is back-loaded into the guidewire lumen 13 by threading the proximal end of the guidewire 23 into the guidewire distal port 16 and proximally through the guidewire lumen common distal section 15, the proximal end of the guidewire 23 will enter the proximal section 14 of the guidewire lumen 13 and not the distal end of the infusion lumen 18 at the junction therebetween because of the small transverse dimension (td) of the crescent-shaped section of the infusion lumen 18. As with other noncircular shapes, the crescent-shaped lumen has a long dimension, typically perpendicular to the small transverse dimension (td), which is longer than (td). However, by having one transverse dimension (i.e., (td) in FIG. 3) that is smaller than the guidewire 23, the restricted passage will prevent the guidewire 23 from sliding into the infusion lumen 18.

The infusion lumen 18 has the noncircular (e.g., crescent) shape at least at the distal end thereof, at the location at which the infusion lumen 18 joins the common distal section 15 of the guidewire lumen 13. In one embodiment, the infusion lumen 18 has the crescent-shape along the entire length of the proximal section 14 of the guidewire lumen 13, but transitions to a circular transverse cross sectional shape proximal thereto (see FIG. 2). The circular proximal section of the infusion lumen extends to the proximal end of the shaft, and connects to a fluid source (not shown) of the agent to be delivered through the infusion lumen. Although the crescent-shaped distal end section of the infusion lumen 18 can be any length, in one embodiment it thus has a length substantially equal to, or within about ±75% of, the length of the proximal section 14 of the guidewire lumen 13 which extends alongside the infusion lumen 18, thus reducing the overall profile in this section. Proximal to the restricted passage, the transverse dimension of the infusion lumen 18 may increase in size and/or become circular in shape. For example, in the illustrated embodiment, the proximal section of the infusion lumen has an inner diameter which is larger than the transverse dimension of the crescent-shaped section of the infusion lumen.

Although the restricted passage between the infusion lumen 18 and the common distal section 15 of the guidewire lumen 13 has a crescent shape in embodiment illustrated in FIG. 3, it should be understood that it can have a variety of suitable transverse cross sectional shapes which are configured to prevent or inhibit passage of the guidewire 23 therethrough. Thus, the noncircular restricted passage can have a variety of suitable shapes including oblong, and semicircular (D-shaped) lumen shapes alternative to the crescent shape of the illustrated embodiment, although a crescent shape is presently preferred due to the relatively large volume but low profile it provides. Additionally, although less preferred due to the relatively small effective lumen volume, the restricted passage can have a circular transverse cross sectional shape with an inner diameter smaller than the outer diameter of the proximal end of the guidewire 23, to thereby not allow it to accommodate the guidewire. Thus, in one embodiment (not shown), the infusion lumen has a transverse cross sectional shape that is circular along the entire length thereof, such that the restricted passage from the infusion lumen to the common distal section of the guidewire lumen is a circular-shaped section of the infusion lumen having a smaller inner diameter than both the common distal section of the guidewire lumen and a circular-shaped proximal section of the infusion lumen.

In the illustrated embodiment, the shaft comprises a first inner tubular member 40 defining the infusion lumen 18, and a second inner tubular member 41 defining the guidewire lumen proximal section 14, and an outer tubular member 42 around the first and second inner tubular members 41, 42, such that the inflation lumen 12 is within the outer tubular member 42. The first inner tubular member 40 has a proximal end at the proximal end of the shaft and a distal end located distal to the guidewire proximal port 17, and the guidewire lumen proximal section 14 is defined by the second inner tubular member 41 having a proximal end at the guidewire proximal port 17 and a distal end located proximal to the distal end of the inflation lumen 12 or balloon 19. Specifically, the second inner tubular member 41 defining the guidewire lumen proximal section 14 has a distal end at the distal end of the restricted passage from the infusion lumen 18 to the common distal section 15 of the guidewire lumen 13, such that the common distal section 15 of the guidewire lumen 13 is defined by a distal section of the first inner tubular member 40. However, the catheter shaft 11 can be made using a variety of suitable designs forming the infusion lumen 12, guidewire lumen proximal section 14, and common distal section 15, including a multilumen extrusion or an alternative arrangement of tubular members.

The balloon 19 has a distal skirt sealingly secured to the first inner tubular member 40 and a proximal skirt sealingly secured to the outer tubular member 42, so that the interior of the balloon is in fluid communication with the inflation lumen 12. In the illustrated embodiment, the inflation lumen 12 has an annular proximal section, an annular distal section, and a crescent-shaped section therebetween along the proximal section 14 of the guidewire lumen 13 (see FIGS. 2-5).

The common distal section 15 of the guidewire lumen is preferably centered along the distal section of the shaft to the distal port 16 of the catheter, and extends coaxially with a distal section of the inflation lumen 12 in the embodiment in which in the catheter is a balloon catheter. A distal tip of the shaft, located distal to an inflatable interior of the balloon, has single lumen circular transverse cross section, with a circular section of the common distal section 15 of the guidewire lumen 13 therein (see FIG. 6), preferably providing a highly maneuverable, flexible distal end section with a round shape unlike multilumen catheter shaft designs having an oblong shaped distal end section. The distal tip of the shaft is typically a soft distal tip member bonded to the end of the shaft inner tubular member to provide an atraumatic distal-leading end, although it can alternatively be formed by the distal end of the shaft inner tubular member itself. The catheter shaft configuration provides a highly maneuverable, flexible, low-profile catheter yet with relatively large sized lumens for excellent performance.

In a method of delivering an agent to a patient's body lumen, the balloon catheter 10 is advanced in the patient's body lumen 30 to position the distal port 16 at a desired treatment location. Typically, the guidewire 23 is first positioned in the body lumen and then the catheter 10 is slidably advanced over the pre-positioned guidewire 23 to the desired treatment location, although the catheter 10 and guidewire 23 can alternatively be advanced together to the treatment location. In either case, the catheter 10 is typically back-loaded onto the guidewire, and preferably advanced into position in the body lumen 30 with the guidewire 23 slidably extending through the full length of the guidewire lumen 13 (proximal and distal sections 14, 15). Thus, the method includes positioning the distal end of the shaft 11 at a desired location in the body lumen, 30 with guidewire 23 slidably disposed in the guidewire lumen 13, the guidewire 23 having a proximal end and a distal end, and extending from the guidewire proximal port 17 to the guidewire distal port 16. After the distal port 16 is thus positioned at a desired treatment location, the method includes infusing an agent into the body lumen from the catheter 10.

Figure 7:
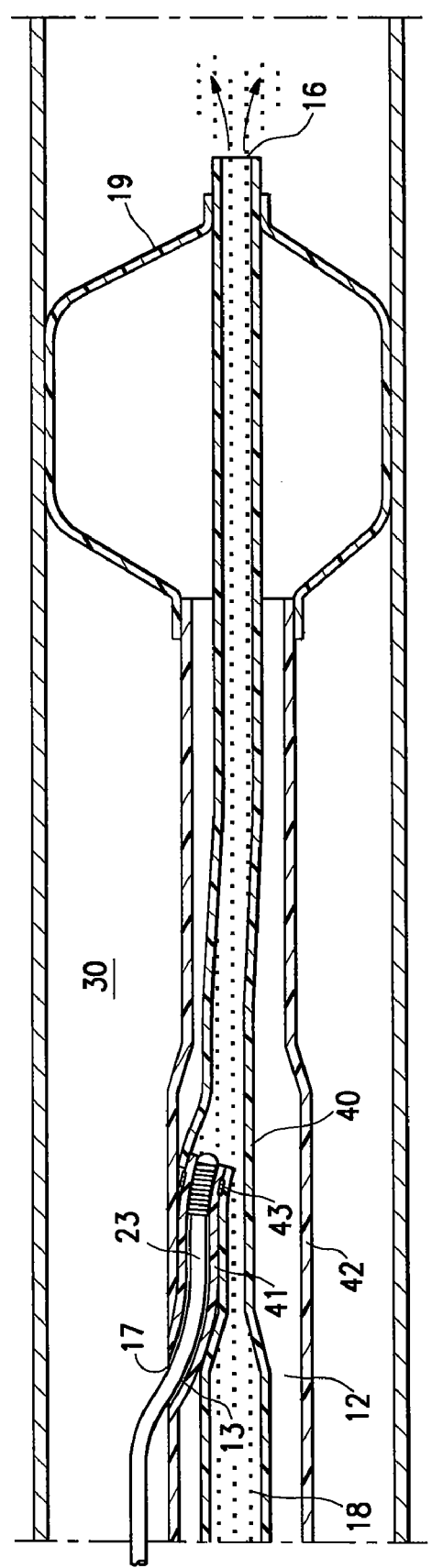
FIG. 7 illustrates the catheter of FIG. 1, with the catheter balloon inflated and the guidewire proximally retracted, during infusion of a fluid into the patient's body lumen.

The balloon 19 is typically in an inflated configuration during the infusion of the agent into the body lumen 30. The inflated balloon preferably anchors the balloon catheter at the desired treatment location, and contributes to containing the agent at the infusion location by occluding the blood flow and preventing the agent from proximally flowing through the body lumen past the inflated balloon. FIG. 7 illustrates the balloon catheter 10 with the balloon 19 inflated in the patient's body lumen 30, during infusion of an agent into the body lumen 30 from the infusion lumen 18.

As illustrated in FIG. 7, the guidewire 23 has been proximally retracted relative to the shaft, so that a distal section of the guidewire is positioned in the proximal section 14 of the guidewire lumen 13 during infusion of the agent. The proximally retracted position of the guidewire 23 preferably positions the distal end of the guidewire within the proximal section 14 of the guidewire lumen 13. As a result, the common distal section 15 is not obstructed by the guidewire 23, but the guidewire remains in position in the guidewire lumen 13 for repositioning or removal of the catheter 10 from the body lumen. The distal end of the proximally retracted guidewire could alternatively extend a short distance into the common distal section 15, provided that at least a substantial length of the common distal section 15 is unobstructed by the guidewire. Thus, in one embodiment, the distal end of the guidewire 23 is distally adjacent to the distal end of the proximal section 14 of the guidewire lumen in the proximally retracted position. A radiopaque material such as a radiopaque marker band 43 on a distal outer surface of the tubular member 41 allows the physician to identify the distal end of the proximal section 14 of the guidewire lumen 13 under fluoroscopy, to facilitate retracting the guidewire 23 to the proximally retracted position.

With the guidewire in the proximally retracted position, a fluid (e.g., a pharmacological agent) is delivered to the patient's body lumen 30, by infusing the fluid through the infusion lumen 18 to the common distal section 15 of the guidewire lumen 13 and out the guidewire distal port 16. Although illustrated with a single agent delivery port 16 at the distal-most end of the shaft 11, it should be understood that one or more additional or alternative agent delivery ports in fluid communication with infusion lumen 18 can be provided in alternative embodiments. For example, agent delivery port (s) proximal to the balloon 19, or between multiple balloons longitudinally spaced-apart on the shaft 11 can be provided to enhance delivery and containment of the fluid agent in the body lumen 30.

The guidewire 23 in the proximally retracted position substantially occludes the proximal section 14 of the guidewire lumen 13, to thereby inhibit the fluid agent from back-flowing proximally out the guidewire proximal port 17 during the infusion of the fluid agent. In a presently preferred embodiment, a conventional guidewire 23 is used with a sufficiently small outer diameter to freely slide within the guidewire lumen proximal section 14 but sufficiently large to substantially occlude the proximal section 14.

Following the infusion of the fluid agent, the balloon 19 is deflated, and the catheter repositioned or removed from the body lumen 30. The catheter 10 and guidewire 23 are longitudinally displaced relative to one another to slidably dispose the guidewire distal end through the guidewire distal port, for repositioning or removing the catheter from the body lumen 30. Thus, the guidewire can be distally advanced into the common distal section 15 of the guidewire lumen 13, or the catheter 10 can be proximally withdrawn from the body lumen 30 while the guidewire 23 is left in place therein, or alternatively, proximally withdrawn together with the guidewire 23 slidably disposed in the guidewire lumen 13.

A variety of suitable agents can be delivered using the catheter(s) and method(s) of the invention, including therapeutic and diagnostic agents. The agents are typically intended for treatment and/or diagnosis of coronary, neurovascular, and/or other vascular disease, and may be useful as a primary treatment of the diseased vessel, or alternatively, as a secondary treatment in conjunction with other interventional therapies such as angioplasty or stent delivery. Suitable therapeutic agents include, but are not limited to, thrombolytic drugs, anti-inflammatory drugs, anti-proliferative drugs, drugs restoring and/or preserving endothelial function, and the like. A variety of bioactive agents can be used including but not limited to peptides, proteins, oligonucleotides, cells, and the like. A variety of diagnostic agents can be used according to the present invention. According to the present invention, agents described herein may be provided in a variety of suitable formulations and carriers including liposomes, polymerosomes, nanoparticles, microparticles, lipid/polymer micelles, and complexes of agents with lipid and/or polymers, and the like.

The dimensions of catheter 10 depend upon factors such as the catheter type and the size of the artery or other body lumen through which the catheter must pass. By way of example, the outer tubular member 42 typically has an outer diameter of about 0.025 to about 0.04 inch (0.064 to 0.10 cm), and a wall thickness of about 0.002 to about 0.008 inch (0.0051 to 0.02 cm), typically about 0.003 to 0.005 inch (0.0076 to 0.013 cm). In one embodiment, a proximal section of the first inner tubular member 40 has an outer diameter of about 0.022 to about 0.05 inch (0.055 to 0.13 cm), and a wall thickness of about 0.002 to about 0.007 inch (0.005 to 0.018 cm), and distal section of the first inner tubular member 40 has an outer diameter of about 0.02 to about 0.04 inch (0.05 to 0.10 cm), and a wall thickness of about 0.001 to about 0.005 inch (0.002 to 0.013 cm). The overall length of the catheter 10 may range from about 100 to about 150 cm, and is typically about 143 cm. Typically, for coronary arteries, balloon 19 has a length about 0.8 cm to about 6 cm, and an inflated working outer diameter of about 2 to about 5 mm.

The dimensions of the lumens 12, 13, 18 and various sections of the catheter shaft 11 depend on a variety of factors including the size of the balloon 19, and the desired end use of the catheter 10, required volume of infusion medium, viscosity of the infusion medium, infusion rate, and size of the guidewire being used. In one embodiment, the diameter of the infusion lumen 18 ranges from about 0.01 to about 0.04 inches, the diameter of the guidewire lumen proximal section 14 is about 0.012 to about 0.04 inches, and the diameter of the guidewire lumen common distal section 15 ranges from about 0.012 to about 0.04 inches. The guidewire lumen 13 is typically sized to accommodate guidewires ranging in size from about 0.01 to about 0.035 inches. The transverse dimension (td) of the restricted passage is typically about 0.008 to about 0.033 inches. The length of the infusion lumen 18 (including the restricted passage) is about 75 to about 120 cm, or about 70 to about 85% of the total length of the catheter 10. In a presently preferred embodiment, the length of the restricted passage is about 2 to about 15 cm, or about 1 to about 10% of the total length of the catheter 10. The length of the guidewire lumen proximal section 14 is preferably about 2 to about 15 cm, and the length of the guidewire lumen common distal section 15 is about 10 to about 25 cm.

The shaft tubular members can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. Although the tubular members 40, 41, 42 are illustrated as single-layered tubes, one or more of the tubular members forming the shaft 11 can be formed of multiple layers or sections of tubing. For example, the outer tubular member 42 is typically formed of two or more tubular sections joined end-to-end, typically providing a stiffness transition along the length of the catheter. In one embodiment, the first inner tubular member 40 is formed of multilayered tubing. The lumen shapes of the shaft tubular members should be understood to refer to the shape provided within normal design tolerances. For example, a circular-shaped lumen is circular or substantially circular within typical tolerances.

While the present invention is described herein in terms of certain preferred embodiments, those skilled in the art will recognize that various modifications and improvements may be made to the invention without departing from the scope thereof. For example, in alternative embodiments the first lumen 12 of the shaft 11 is configured for a purpose other than inflation of a balloon on the shaft 11. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

I claim:

1. An infusion balloon catheter, comprising:
    a) an elongated shaft having a proximal end, a distal end, an inflation lumen, an infusion lumen that is disposed therein and that extends distally to a distal port and a guidewire lumen for receiving a guidewire having a diameter, that extends distally from a guidewire proximal port formed in said shaft at a position that is spaced distally from the proximal end of said shaft, wherein said guidewire lumen extends along a length of an inner wall of said infusion lumen distal to said proximal port to merge with said infusion lumen in a substantially parallel configuration at a location proximal to said distal port, wherein said infusion lumen has a restricted passage adjacent to said guidewire lumen, such restricted passage having a transverse dimension that is smaller than said guidewire diameter, wherein said infusion lumen distal to said guidewire lumen is capable of accommodating a guidewire as well as a flow of infusion fluid and wherein said restricted passage prevents a guidewire that is being back-loaded through said distal port from extending through said infusion lumen beyond its merger with said guidewire lumen; and
    b) an inflatable balloon on a distal section of the elongated shaft, having an interior in fluid communication with the inflation lumen.

2. The balloon catheter of claim 1 wherein the restricted passage is a crescent-shaped section of the infusion lumen extending along at least a portion of the guidewire lumen.

3. The balloon catheter of claim 2 wherein the infusion lumen has a circular-shaped proximal section located proximal to the crescent-shaped section.

4. The balloon catheter of claim 3 wherein the proximal section of the infusion lumen has an inner diameter which is larger than the transverse dimension of the crescent-shaped section of the infusion lumen.

5. The balloon catheter of claim 3 wherein the crescent-shaped section of the infusion lumen has a proximal end, a distal end and a length extending from the proximal to the distal end thereof, and the length of the crescent-shaped section is substantially equal to the length of the guidewire lumen which extends alongside the infusion lumen.

6. The balloon catheter of claim 1 wherein the restricted passage is a noncircular section of the infusion lumen extending along at least a portion of the guidewire lumen.

7. The balloon catheter of claim 1 wherein the infusion lumen has a circular transverse cross sectional shape along its entire length, such that the restricted passage is a circular-shaped section of the infusion lumen having a smaller inner diameter than sections proximal and distal thereto.

8. The balloon catheter of claim 1 wherein the inflation lumen has an annular proximal section, an annular distal section, and a crescent-shaped section therebetween along the guidewire lumen.

9. The balloon catheter of claim 1 wherein a distal tip of the shaft distal to an inflatable interior of the balloon has a single lumen with a circular transverse cross section with a circular section of the infusion lumen therein.

10. A method of treating a site in a patient's body lumen, comprising:
    a) providing an infusion balloon catheter comprising an elongated shaft having a proximal end, a distal end, an inflation lumen, a guidewire lumen which has a proximal section and a common distal section and which extends from a guidewire distal port at the shaft distal end to a guidewire proximal port spaced distally from the proximal end of the shaft, and an infusion lumen which is in fluid communication with the guidewire distal port, wherein said guidewire lumen extends along a length of an inner wall of said infusion lumen distal to said proximal port to merge with said infusion lumen at a location distal to the guidewire proximal port and proximal to a distal end of the inflation lumen, wherein the infusion lumen has a restricted passage adjacent to said guidewire lumen having a smaller transverse dimension than the guidewire lumen so as to prevent the proximal end of a guidewire from slidably extending proximally therethrough into the infusion lumen, and a balloon on a distal section of the elongated shaft having an interior in fluid communication with the inflation lumen;
    b) threading a guidewire proximal end into the guidewire distal port, through the guidewire lumen and out the guidewire proximal port;
    c) advancing said catheter along said guidewire through the patient's body lumen and positioning the distal end of the shaft at a desired location in the body lumen; and
    d) proximally retracting the guidewire relative to the shaft to position a distal section of the guidewire in the proximal section of the guidewire lumen, and delivering a fluid to the patient's body lumen with the guidewire in the proximally retracted position, by infusing the fluid through the infusion lumen to the common distal section of the guidewire lumen and out the guidewire distal port.

11. The method of claim 10 wherein the restricted passageway has a transverse cross section with a crescent-shape which is narrower in a first direction than in a perpendicular second direction, and the guidewire proximal end has a circular transverse cross section with a larger diameter than the narrower first direction of the crescent-shaped restricted passageway such that the guidewire proximal end is prevented from entering the infusion lumen by the restricted passage.

12. The method of claim 10 wherein the guidewire in the proximally retracted position substantially occludes the proximal section of the guidewire lumen to thereby inhibit the fluid from back-flowing proximally out the guidewire proximal port, and including longitudinally displacing the guidewire in the guidewire lumen after c) to slidably dispose the guidewire distal end through the guidewire distal port.

13. The method of claim 10 including inflating the balloon after c) and before d).

* * * * *